United States Patent [19]

Juguin et al.

[11] Patent Number: 4,544,791

[45] Date of Patent: Oct. 1, 1985

[54] PROCESS FOR PRODUCING PREMIUM GASOLINE BY POLYMERIZING C$_4$ CUTS

[75] Inventors: Bernard Juguin, Rueil-Malmaison; Jean Miquel, Paris, both of France

[73] Assignee: Institut Francais du Petrole, Rueil-Malmaison, France

[21] Appl. No.: 623,672

[22] Filed: Jun. 22, 1984

[30] Foreign Application Priority Data

Jun. 22, 1983 [FR] France ............................ 83 10431

[51] Int. Cl.$^4$ ............................................... C07C 2/02
[52] U.S. Cl. .................................... 585/517; 585/525; 585/533
[58] Field of Search ................... 585/517, 525, 533

[56] References Cited

U.S. PATENT DOCUMENTS 3,311,672 3/1967 Kovach ................................ 585/525
4,465,887 8/1984 Schammel ........................... 585/517

*Primary Examiner*—Curtis R. Davis
*Attorney, Agent, or Firm*—Millen & White

[57] ABSTRACT

The invention relates to a process for producing premium gasoline from olefinic C$_4$ cuts containing 1- and 2-butenes and isobutene, the process consisting of converting at least 97% of the total isobutene content of the charge and at least the major portion of the 1- and 2-butenes thereof to C$_4$ hyrocarbons dimers and trimers without producing substantial amounts of kerosene, said process being characterized in that, in a first step, the olefinic C$_4$ cut is treated in a first polymerization catalytic zone so as to convert at least 80% of the isobutene to isobutene dimers and trimers and to convert at most 45% of the mixture of 1- and 2-butenes to dimers and trimers thereof, in that, subsequently, the effluent from said first catalytic polymerization zone is fractionated so as to recover, on the one hand, from the column bottom, essentially the C$_4$ olefinic hydrocarbon dimers and trimers and, on the other hand, from the top of the column, a mixture containing the major part of the isobutene and 1- and 2-butenes not converted in said first catalytic polymerization zone, said mixture being, during a second step, at least partly fed to a second catalytic polymerization zone so as to convert (a) substantially the total amount of isobutene to isobutene dimers and trimers in said second zone and (b) at least 50% of the 1- and 2-butenes, supplied to said second zone to n-butenes dimers and trimers.

12 Claims, 3 Drawing Figures

PROCESS FOR PRODUCING PREMIUM GASOLINE BY POLYMERIZING C$_4$ CUTS

BACKGROUND OF THE INVENTION

This invention concerns a process for producing premium gasoline by polymerizing C$_4$ cuts, then adding value to C$_4$ olefinic cuts available in large amounts on the market as a result of the developing processes of naphtha and gas oils steam-cracking and catalytic cracking.

Olefins, butenes and isobutenes may be used in petrochemical syntheses of more elaborate products (alcohols, aldehydes, acids, nitriles, etc.), but the available amounts of these C$_4$ cuts are generally too large or at least may become too large for having their use limited to said first way of adding value to the C$_4$ cuts.

A second way of adding value to a C$_4$ cut consists of recycling this C$_4$ cut to the cracking unit (steam-cracking or catalytic cracking unit) after hydrogenation of the olefins; but here, the isobutane contained in the hydrogenated cut, not exceeding 50% by weight of said cut, does not give sufficiently high yields to ethylene and also results in a substantial production of methane which cannot be used to a large extent, except as fuel.

A third way of adding value to a C$_4$ cut consists, after hydrogenation of said cut, of separating the n-butane from the isobutane by distillation and recycling to the steam-cracking unit only the n-butane, while keeping the isobutane for other more advantageous uses, such as for producing, for example, isoparaffinic gasolines by alkylation. However, the ethylene and propylene yields, in such a steam-cracking, do not exceed 38 and 20% respectively, by weight, and the methane production is about 25% by weight.

A fourth way of adding value to a C$_4$ cut consists of alkylating the olefins of said cut with the isobutane contained therein, so as to obtain a maximum yield of gasolines. However, in this alkylation step, the isobutene behaviour is less favorable than that of the butenes for obtaining a gasoline of high octane number; as a matter of fact, the Research (or Clear) octane numbers of normal butenes are higher than those of isobutene alkylates.

It still exists other ways, for example, that consisting of converting the isobutene of the charge to isobutene di- and trimers without substantially modifying the butenes of the charge, of subsequently isomerizing the 1-butene of the charge to 2-butene in view of subsequently subjecting the 2-butene to an alkylation reaction with isobutane (U.S. Pat. No. 4,392,002).

Another method would consist in a modification of this latter technique according to which the totality of the butenes present in the initial charge are converted to isobutene dimers and trimers, which products form an excellent motor fuel.

This method is performed (see, for example, the French Pat. No. 2,515,171), by subjecting the charge, (olefinic C$_4$ cut), to a polymerization during which the isobutene is converted, in a proportion of 90% by weight or more, to dimers and trimers, which are separated from the unconverted butenes by mere fractionation and fed to the gasoline pool. The normal butenes (unreacted or having only reacted to a small extent during the polymerization), are then separated and the C$_4$ paraffinic hydrocarbons extracted therefrom can be fed to the gasoline pool. The fraction subjected to extraction has a very high content of n-butenes (at least 99% by weight) and those n-butenes are converted by isomerization to isobutene which, in turn, will be converted to isobutene dimers and trimers.

By this way, the totality of the initial olefinic C$_4$ cut can be converted to gasoline.

SUMMARY OF THE INVENTION

Now, it has been discovered that it could be appropriate to modify this latter technique in the following manner, consisting of converting the major part of the butenes contained in the initial charge to dimers and trimers of the initial butenes, which are known as forming an excellent motor fuel, (at the end of the process, at least 90% of the 1-butene, at least 80% of the 2-butene and at least 97% of the isobutene of the initial olefinic C$_4$ cut are thus converted without forming substantial amounts of kerosene).

The process object of the present invention thus consists of first subjecting the charge (olefinic C$_4$ cut), generally made free of at least the major part of the butadiene initially contained therein, to a first polymerization reaction during which the total conversion rate of the normal butenes contained in the charge remains lower than 45% by weight and during which at least 80%, by weight, (preferably at least 85%) of the present isobutene are converted, these hydrocarbons being essentially converted to dimers and trimers; then, the product discharged from the reactor is subjected to a fractionation in order to obtain, on the one hand, a first fraction containing unreacted isobutene and butenes, (which is fed at least partly to a second polymerization zone (different from the first polymerization zone) wherein the operating conditions are so selected as to obtain the best conversion of normal butenes to dimers and trimers, which operation will be described hereinafter) and, on the other hand, a second fraction consisting essentially of dimers and trimers, (of isobutene), which is fed to the gasoline pool.

Thus, the first fraction of very high content of unreacted normal butenes, and the remaining unconverted part of isobutene are fed together to a second isomerization reactor where the olefins are converted in major part to dimers and trimers thereof. Pratically 100% of the isobutene and at least 50% by weight of the 1- and 2-butenes are converted and, preferably, at least 75% by weight of the 1-butene and more than 55% by weight of the 2-butene are converted in this reactor.

The operation may be conducted in two different manners: In a first manner, the product issuing from the second polymerization reactor, still containing, in addition to the produced dimers and trimers, a certain amount of unreacted C$_4$ olefins, is fed, jointly with the product issuing from the first polymerization reactor, to the fractionation column so as to separate the obtained dimers and trimers from the unreacted C$_4$ olefins.

The second operating manner, also in conformity with the present invention, consists of feeding the product issued from the second polymerization reactor, operated as above, to a second fractionation column, separate from the first column, so as to obtain, on the one hand, a first fraction containing unreacted normal butenes and, on the other hand, a second fraction formed by dimers and trimers of the butenes (unreacted normal butenes and isobutenes of the first polymerization reactor). The major part of the first fraction is recycled to the second polymerization reactor, after withdrawal of an aliquot part thereof, smaller than about 20% by weight, which is fed to the gasoline pool, the purpose of this operation being to facilitate the removal of the paraffinic hydrocarbons contained in the charge. The second fraction is fed to the gasoline pool.

BRIEF DESCRIPTION OF THE DRAWINGS

The process corresponding to the invention, with its two alternative embodiments, is diagrammatically illustrated by the accompanying FIGS. 1 and 2.

DETAILED DESCRIPTION OF THE INVENTION

Figure 1:
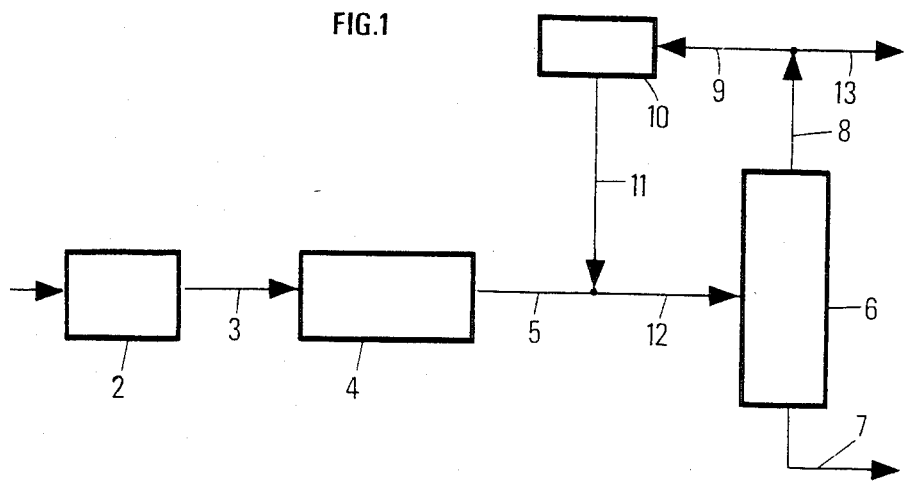

First embodiment (FIG. 1): An olefinic $C_4$ cut, which generally, at this stage, contains isobutane, n-butane, 1-butene, 2-butene, isobutene and a small amount, if any, of propene and/or butadiene (generally less than 2% and preferably less than 0.7% by weight of propene and butadiene) is introduced, through line 1, into an optional drying zone 2. This drying can be performed in a conventional manner, for example, by passing the cut over alumina or a molecular sieve, preferably a sieve of 3A type. The so-dried cut is fed, through line 3, to a polymerization zone 4 wherein the major part of the isobutene contained in the charge is essentially converted to isobutene dimers and trimers.

In said polymerization zone, the operating conditions are such that isobutene reacts up to conversion rates higher than 80%, or even 82% by weight, preferably 85% or even 95%, while the total conversion rate of the normal butenes remains lower than 45% by weight.

The polymerization reactions are generally performed in the presence of a catalyst arranged, for example, as a fixed bed, at a temperature of about 40° to 250° C., under a pressure of about 0.1 to 10 MPa (about 1 to 100 bars); preferably, the temperature is about from 45° to 200° C. and the pressure from 0.1 to 5 MPa; the flow rate of liquid hydrocarbons (space velocity) is about from 0.05 to 5, preferably from 0.8 to 2.5 volumes per volume of catalyst and per hour.

In said first polymerization zone 4, the operating conditions will be sweeter than in the second zone 10, so as to prevent a more extensive polymerization of isobutene, i.e., in order to avoid the production of hydrocarbons having more than 12 carbon atoms per molecule.

The catalyst of acid type may be a silica alumina or a boron alumina or boron-containing alumina. The selected catalyst may also be obtained by treatment of a transition alumina by means of at least one fluorine acid derivative, optionally with addition of a silicic ester. The catalysts used according to the present invention for the polymerization reaction show qualities superior to those of other polymerization catalysts such as sulfuric acid or still phosphoric acid. These types of catalysts are used in U.S. Pat. No. 2,298,330 but result, during the polymerization of isobutene, in the parasitic formation of heavy gasoline. When using phosphoric acid, this acid may be deposited on Kieselguhr or on silica, or on quartz, or may be of the "solid phosphoric acid" type, (catalyst consisting of a siliceous material of high absorbing power impregnated with a high proportion of phosphoric acid).

According to the invention, a preferred catalyst is a silica alumina whose silica content ranges from 60 to 95% by weight and preferably from 70 to 90%, with the optional addition of 0.1 to 0.5% of chromium oxide and/or zinc oxide. The specific surface of the silica alumina may advantageously range from 50 to 500 $m^2$ per gram, preferably from 150 to 400 $m^2/g$, its pore volume being, for example, from 0.40 to 0.90 cc/gram.

The polymerization effluent is withdrawn through lines 5 and 12.

After separation, by distillation in column 6, of the dimers and trimers (of the obtained isobutene and butenes) which are conveyed through line 7 to the gasoline pool, the unreacted isobutene and butenes are recovered through line 8, together with the paraffinic hydrocarbons contained in the crude charge, a first portion (generally not exceeding 30% by weight of the $C_4$ hydrocarbons discharged from the top of the column) is fed through line 13 to the gasoline pool, the purpose of this separation being to remove the excess of paraffinic hydrocarbons which otherwise would accumulate in the recycle gas, and a second portion, the more substantial, is fed, through line 9, to a second polymerization zone 10, wherein the pressure and temperature conditions are more severe than in the first polymerization zone (4) (i.e. the input temperature and the output temperature of the second polymerization zone are each from 20° to 60° C. and preferably 30° to 50° C. higher than the input and output temperatures of the first polymerization zone and the pressure in the second polymerization zone is from 0.4 to 3 MPa and preferably, 0.8 to 2 MPa higher than the pressure prevailing in the first polymerization zone), and wherein the $C_4$ olefins are converted to isobutene and butenes dimers and trimers; the conversion rate of residual isobutene is 100%; the conversion of 1-butene may reach 80%, whereas the total conversion of 2-butenes does not exceed 60% by weight.

The obtained products as well as the unreacted gases discharged from the polymerization zone 10 are fed, through line 11, jointly with the product discharged through line 5 from the first polymerization zone 4, to the distillation zone 6.

Second embodiment (FIG. 2): Elements 1 to 7 of FIG. 2 have the same definition as elements 1 to 7 of FIG. 1. In this embodiment, the gaseous products issuing from the fractionation zone 6, through lines 8 and 9, are fed entirely to the second polymerization zone 10 where the conversions are substantially the same as in the case of the first embodiment. After reaction, the products issuing from said zone through line 11, instead of being recycled to the distillation zone 6, as in the first embodiment, are introduced in a second distillation zone 12, wherein the dimers and trimers of the obtained $C_4$ olefins are separated from the unreacted paraffinic hydrocarbons and olefins and fed, through lines 13 and 16, to the gasoline pool, jointly with the dimers and trimers issuing from the distillation column 6 through line 7.

The gases discharged from the top of column 12 and consisting exclusively of residual butenes, together with the paraffinic hydrocarbons introduced by the initial charge, are divided into two parts. A first part (which will not exceed 30% by weight of the $C_4$ hydrocarbons discharged from the top of the column) is fed, through lines 17 and 14, to the gasoline pool. As in the first embodiment, the purpose of this separation is to remove the excess of paraffinic hydrocarbons. The second part, more substantial, is recycled through line 15 to the second polymerization zone 10.

In view of the high exothermicity of the polymerization conversion in zone 4, it will be preferable to limit the isobutene content of the charge to at most about 45% by weight since, otherwise, it should have to be diluted, for example with butane or isobutane and/or for example with a portion or the totality of the C$_4$ hydrocarbons of high butanes content, discharged from line 13, in the case of the first embodiment or from line 14 in the second embodiment, of the effluent separated at the top of the distillation columns 6 or 12 respectively.

Figure 2:
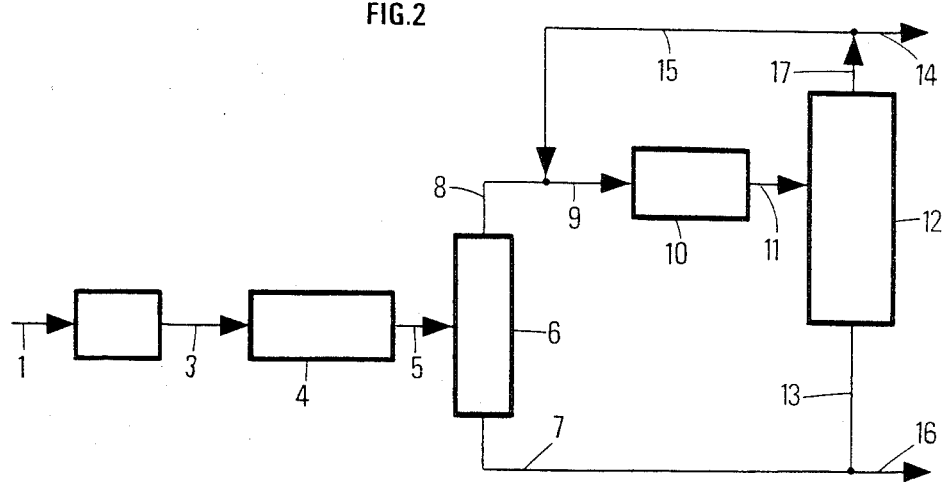

This recycled fraction of high butanes content will be fed to the first polymerization zone 4 in both cases (FIGS. 1 and 2).

The dilution may also be performed by means of fresh isobutane (and/or butane).

EXAMPLE 1: (illustrating FIG. 1)

By way of example, a steam-cracking olefinic C$_4$ cut from which butadiene has been extracted, is subjected to the treatment.

The composition of the charge is given, in percent by weight, in Table A.

TABLE A

| Composition of the charge (% by weight) | |
|---|---|
| Propyne | 0.05 |
| Isobutane | 1.47 |
| n-butane | 7.89 |
| Isobutene | 39.42 |
| 1-butene | 28.76 |
| Σ 2-butenes | 22.15 |
| 1-3 butadiene | 0.26 |

The charge is first subjected to drying over a 3A molecular sieve (zone 2 of the figure) and then it is fed through line 3 to the butenes polymerization zone 4.

The polymerization reaction takes place in the presence of a silica-alumina catalyst of 90% by weight silica content, having a specific surface of 420 m$^2$/g and a pore volume of 0.40 cc/g.

The operating conditions are as follows:

| Pressure | 1.2 MPa |
|---|---|
| Temperature at the reactor input | 55° C. |
| Temperature at the reactor output | 75° C. |
| Space velocity (VVH) | 2 h$^{-1}$ |

The reaction develops in the liquid phase.

The obtained effluent is subjected to fractionation, (zone 6 of the figure), jointly with the recycled products, fed through line 11, from the second polymerization reactor 10.

A polymerizate is recovered from the column bottom through line 7. It amounts to 84.28% by weight of the initial charge and consists exclusively of C$_4$ hydrocarbons dimers and trimers. 45.03% of the latter have been produced in the polymerization zone 4 and the complementary amount to 84.28%, i.e. 39.25%, results from the products obtained in the second polymerization zone 10. It is noticeable that polymers having more than 12 carbon atoms per molecule are absent.

The fraction obtained through line 8, at the top of the column, has the following composition in percents by weight with respect to the initial charge:

| Butane + Isobutane | 93.60 |
|---|---|
| Isobutene | 5.12 |
| 1-butene | 22.45 |
| Σ 2-butenes | 35.88 |
| 1-3 butadiene | 0.08 |

10% by weight of the total gaseous effluent from the top of the column is withdrawn in order to avoid an excessive accumulation of paraffinic C$_4$ hydrocarbons in the recycle loop. Said withdrawn amount is fed, through line 13, to the gasoline pool, but it may also be recycled to the polymerization zone 4, when necessary, for reducing the reaction exothermicity.

The remaining 90% by weight of the effluent, still containing non negligible quantities of butenes, which, in the present example, amount to 40.38% by weight of the effluent, are fed through line 9 to the second polymerization zone 10 containing the same catalyst as the first zone 4, but wherein the operating conditions are more severe in order to favour the conversion of straight-chain butenes (1- and 2-butenes).

In said second reactor 10, the operating conditions are as follows:

| Pressure | 2.5 MPa |
|---|---|
| Temperature at the reactor input | 95° C. |
| Temperature at the reactor output | 115° C. |
| Space velocity (VVH) | 1 h$^{-1}$ |

Here, the reaction also takes place in the liquid phase.

The reaction product, issuing from reactor 10 through line 11, no longer contains isobutene or butadiene, which have been completely converted to polymers, and it has the following composition in percents by weight with respect to the initial charge:

| Butane + Isobutane | 84.24 |
|---|---|
| 1-butene | 4.04 |
| Σ 2-butenes | 13.88 |
| Dimers and trimers of isobutene and of n-butenes | 39.25 |

This effluent is fed, jointly with that issuing from the first polymerization reactor 4, to the fractionation zone 6. During this second step, substantially 100% of the isobutene, about 78% of the 1-butene and 58% of the 2-butenes of the initial charge have been converted to isobutene and normal butenes, dimers and trimers.

The main characteristics of the gasoline cut obtained at the bottom of the fractionation column 6, which is fed, through line 7, to the gasoline pool, and which amounts to 84.28% by weight of the initial charge, are as follows:

| Density at 20° C. | 0.739 |
|---|---|
| Bromine number | 111 |
| Octane number RON clear | 99.5 |
| ASTM distillation | |
| IP | 60° C. |
| 5% | 104° C. |
| 10% | 108° C. |
| 20% | 109° C. |
| 30% | 111° C. |
| 40% | 113° C. |
| 50% | 118° C. |
| 60% | 125° C. |
| 70% | 137° C. |
| 80% | 156° C. |
| 90% | 189° C. |
| 95% | 193° C. |
| FP | 213° C. |

-continued

| | |
|---|---|
| Distillate | 100% |
| Residue | 0 |
| Losses | 0 |

The specifications concerning the final points of the gasolines are recalled hereinafter:

| | |
|---|---|
| Japan | 225° C. |
| USA | 220° C. |
| France | 215° C. |

EXAMPLE 2: (illustrating FIG. 2)

Here the charge to be treated is the same as in the preceding example. The catalyst is the same. The operating conditions in the two polymerization reactors 4 and 10 are also the same as in the preceding example.

The only difference is in the arrangement of the apparatus. As a matter of fact, in this example, an additional distillation column 12 is used for independently distilling the effluents from reactors 4 and 10. The volume of recycled product is thus decreased.

This arrangement requires the use of two distillation columns which, accordingly, will generally be of a smaller size than the column of FIG. 1.

The effluent from the polymerization zone 4 is fed, through line 5, to the fractionation column 6. A polymerizate is recovered from the bottom of the column, through line 7. This polymerizate amounts to 45.03% by weight of the initial charge and forms a gasoline of premium grade.

The fraction obtained through line 8, from the top of the column, has the following composition, in percents by weight with respect to the initial charge:

| | |
|---|---|
| Butane + Isobutane | 9.36% |
| Isobutene | 5.12% |
| 1-butene | 18.41% |
| Σ 2-butenes | 22.15% |
| 1-3 butadiene | 0.08% |

This effluent, consisting exclusively of C$_4$ hydrocarbons, is fed, through line 8, to a second polymerization zone 10, jointly with a second effluent, consisting of C$_4$ hydrocarbons separated at the top of the second distillation column 12 and fed through line 15.

This second effluent, containing only normal butenes and butanes, has the following composition, in percents by weight with respect to the initial charge:

| | |
|---|---|
| Butane + Isobutane | 37.20% |
| 1-butene | 3.45% |
| Σ 2-butenes | 11.52% |

The product discharged from the second polymerization zone 10 is fed, through line 11, to a second fractionation column 12.

A polymerizate is recovered, through line 13, from the column bottom. It amounts to 41.83% by weight of the initial charge, which exclusively consists of C$_4$ olefinic hydrocarbons dimers and trimers and is fed, jointly with the polymerizate from the bottom of the column 6 (amounting to 45.03% by weight of the initial charge) to the gasoline pool.

As a whole, there is thus obtained 86.86% by weight of gasoline of premium grade.

From the top of the column, an effluent is withdrawn whose composition, in percents by weight of the initial charge, is as follows:

| | |
|---|---|
| Butane + Isobutane | 41.77% |
| 1-butene | 4.37% |
| Σ 2-butenes | 14.42% |

20% by weight of the total effluent issuing from the top of the column, corresponding to 13.14% by weight of the initial charge, are withdrawn and the remaining fraction recycled, through line 15, to the second polymerization reactor 10. Said effluent, which is fed to the gasoline pool, has the following composition in percent by weight:

| | |
|---|---|
| Butane + Isobutane | 71.23% |
| 1-butene | 6.85% |
| Σ 2-butenes | 21.92% |
| | 100% |

The remaining 80% by weight of said effluent, corresponding to 52.17% by weight of the initial charge, and containing 28.77% by weight of polymerizable butenes, are recycled, through line 15, to the second polymerization zone 10, where they are added to the effluent, fed through line 8, from the first distillation zone 6.

During said second step, substantially 100% of the isobutene, about 80% of 1-butene and 60% of the 2-butenes of the initial charge have been converted to isobutene dimers and trimers.

EXAMPLE 3: (comparative, illustrated by FIG. 3)

Figure 3:
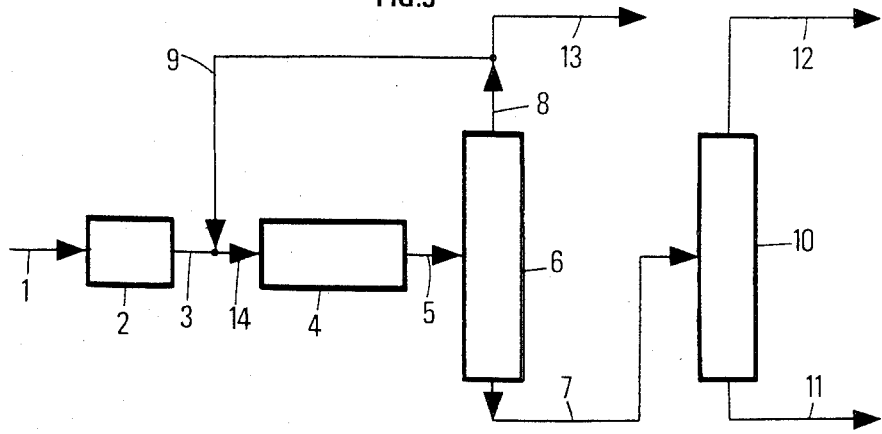
FIG. 3 illustrates a conventional manner of polymerizing butenes.

As shown in FIG. 3, which illustrates the usual way of polymerizing butenes, a single reactor is used.

The charge and the catalyst are the same as those used in the two preceding examples.

The charge (line 1) is first dried by passage through a 3A molecular sieve (zone 2 of the figure), then fed through line 3 and 14, jointly with the recycled hydrocarbons supplied through line 9, to the polymerization zone 4.

In this reactor, the operation conditions are as follows:

| | |
|---|---|
| Pressure | 2.5 MPa |
| Temperature at the reactor input | 95° C. |
| Temperature at the reactor output | 115° C. |
| Space velocity (VVH) | 1 h$^{-1}$ |

The reaction here also takes place in the liquid phase.

The product issuing from the reaction zone 4 is fed, through line 5, to a first distillation column 6, where it is subjected to fractionation.

A polymerizate is recovered, through line 7, from the column bottom. It amounts to 87.67% by weight of the initial charge, containing, in addition to dimers and trimers, heavier constituents.

The characteristics of this product are as follows:

| | |
|---|---|
| Density (20° C.) | 0.763 |
| Bromine number | 82 |
| Clear octane number | 97.5 |
| ASTM Distillation | |

-continued

| | |
|---|---|
| IP | 78° C. |
| 5% | 112° C. |
| 10% | 116° C. |
| 20% | 121° C. |
| 30% | 128° C. |
| 40% | 138° C. |
| 50% | 151° C. |
| 60% | 169° C. |
| 70% | 185° C. |
| 80% | 203° C. |
| 90% | 238° C. |
| 95% | 249° C. |
| FP | 270° C. |
| Distillate | 98% |
| Residue | 2% |
| Losses | 0 |

The French standards limit the final distillation point of motor gasolines to 215° C. so that it will be necessary to subject this product to a further fractionation as described below.

From the top of the column, a fraction is obtained, through line 8, which consists of unreacted $C_4$ paraffins and olefins whose composition, in percents of the initial charge, is as follows:

| | |
|---|---|
| Butane + Isobutane | 93.36 |
| 1-butene | 1.16 |
| Σ 2-butenes | 28.46 |

10% by weight of this effluent is discharged in order to remove the $C_4$ paraffins which, otherwise, would continuously accumulate, since they do not react.

This discharged amount of high butane content (75.91% by weight) is fed, mainly through line 13, to the gasoline pool. The reamining 90% are recycled, through line 9, to the polymerization reactor 4, where they join the fresh charge.

The product recovered at the column bottom (distillation zone 6) which is not conform with the French specifications concerning the ASTM final distillation point, is fed, through line 7, to the second distillation zone 10.

A premium gasoline cut, amounting to 72.76% by weight of the fresh charge, is obtained at the top of said column and fed, through line 12, to the gasoline pool. A kerosene cut, amounting to 14.91% by weight of the initial charge, is withdrawn, through line 11, from the bottom of the column. After hydrogenation, it can be used as jet fuel.

TABLE I

| EXAMPLE | 1 | 2 | 3 (comparative) |
|---|---|---|---|
| $C_4$ hydrocarbons fed to the gasoline pool | 15.72 | 13.14 | 12.33 |
| Premium gasoline (isobutene dimers and trimers) | 84.28 | 86.86 | 72.76 |
| Kerosene (to be hydrogenated) | — | — | 14.91 |
| TOTAL | 100 | 100 | 100 |

It is observed that the processes according to FIGS. 1 and 2 give far higher yields of directly usable premium gasoline that the conventional process of FIG. 3 (comparative).

By using two successive reactors, it is possible to proceed under optimum operating conditions in each of them, thus avoiding a too extensive polymerization of isobutene, resulting in the formation of too heavy hydrocarbons which can not be used as motor fuel.

Table II gives the olefins total conversion rates for each of the three examples.

TABLE II

| EXAMPLE | 1 | 2 | 3 |
|---|---|---|---|
| Propyne | 100% | 100% | 100% |
| Isobutene | 98.71 | 100% | 100% |
| 1-butene | 92.18 | 96.87 | 96.1 |
| 2-butenes | 83.79 | 87 | 40.4 |
| 1-3 butadiene | 96.15 | 100 | 100 |

EXAMPLE 4 (comparative)

Example 2 is repeated in the same operating conditions. However the catalyst used in the two polymerization zones 4 and 10, is no longer silica alumina, but a solid mixture of phosphoric acid and silica (containing by weight 68% of $P_2O_5$ and 32% of $SiO_2$), said catalyst being used as extrudates of 5 to 6 mm diameter and having the following characteristics:

| | |
|---|---|
| Particle density | 1.99 |
| Structural density | 2.99 |
| Total pore volume | 0.11 cm$^3$/g |
| Specific surface | 6.5 m$^2$/g |

When starting the operation, the isobutene conversions to dimers and trimers in the first polymerization zone 4 are appropriate and substantially the same as in example 2, but, in the second polymerization zone 10, the conversion rate of n-butenes is low, so that the polymerizate, withdrawn through line 13 from the fractionation zone 12, amounts only to 23.50% of the total weight of the charge, instead of 45.03% in example 2.

Then the catalyst in the two polymerization zones 4 and 10 quickly losses its activity as a result of the formation of alkyl phosphate which leads to a quick degradation of the catalyst by drawing away phosphoric acid.

In order to cope with this disadvantage, it would be then convenient to proceed, in each of the two polymerization zones, at a temperature of 200° C. and under a pressure of 4 MPa (i.e. under not desirable conditions). Such conditions give a polymerizate amounting to 77.15% by weight of the initial charge (86.86% in example 2), but result in the formation of 9.71% by weight (for both polymerization zones 4 and 10) with respect to the initial charge, of a heavy product boiling above 235° C. and consisting of $C_{12}{}^+$ polymers of isobutene and n-butenes.

What is claimed as the invention is:

1. A process for producing premium gasoline from olefinic $C_4$ cuts containing 1- and 2-butenes and isobutene and made free of at least a major part of the butadiene initially contained therein, the process consisting of converting at least 97% of the total isobutene content of the charge and at least the major portion of the 1- and 2-butenes thereof to $C_4$ hydrocarbons dimers and trimers without producing substantial amounts of kerosene, said process comprising, in a first step, treating the olefinic $C_4$ cut in a first so-called polmerization catalytic zone, at input and output temperatures ranging from 40° to 250° C., under a pressure from 0.1 to 10 MPa, with a flow rate of liquid hydrocarbons (space velocity) from about 0.05 to 5 volumes per volume of catalyst and per hour, in the presence of a catalyst selected from the group consisting of silica-aluminas, boron-containing aluminas and transition aluminas treated with at least one fluorine acid derivative, so as to convert at least 80% of the isobutene to isobutene dimers and trimers and to convert at most 45% of the mixture of 1- and 2-butenes to dimers and trimers thereof, in that, subsequently, fractionating the effluent from said first catalytic polymerization zone so as to recover, on the one hand, from the column bottom, essentially the $C_4$ olefinic hydrocarbons dimers and trimers and, on the other hand, from the top of the column, a mixture containing the major part of the isobutene and 1- and 2-butenes not converted in said first catalytic polymerization zone, feeding said mixture, during a second step, at least partly to a second catalytic polymerization zone operating at input and output temperatures from 40° to 250° C., under a pressure from 0.1 to 10 MPa and with a flow rate of liquid hydrocarbons (space velocity) from about 0.05 to 5 volumes per volume of catalyst and per hour, the input and output temperatures of the second polymerization zone being each from 20° to 60° C. higher than the input and output temperatures of the first polymerization zone, the pressure in the second polymerization zone being from 0.4 to 3 MPa higher than the pressure in the first polymerization zone, in the presence of a catalyst selected from the group consisting of silica-aluminas, boron-containing aluminas and transition aluminas treated with at least one fluorine acid derivative, so as to convert (a) substantially the total amount of isobutene to isobutene dimers and trimers in said second zone and (b) at least 50% of the 1- and 2-butenes, supplied to said second zone, to n-butenes dimers and trimers.

2. A process according to claim 1, wherein, during the second catalytic polymerization step, at least 75% of the 1-butene and 55% of 2-butene are converted to dimers and trimers.

3. A process according to claim 1, wherein the two polymerization zones operate at input and output temperatures ranging from 45° to 200° C., under a pressure from 0.1 to 5 MPa, with a flow rate of liquid hydrocarbons from about 0.8 to 2.5 volumes per volume of catalyst and per hour, the input and output temperatures of the second polymerization zone being each from 30° to 50° C. higher than the input and output temperatures of the first polymerization zone, the pressure in the second polymerization zone being from 0.8 to 2 MPa higher than the pressure in the first polymerization zone.

4. A process according to claim 1, wherein, during the first step, at least 85% of the isobutene are converted to isobutene dimers and trimers.

5. A process according to claim 1, wherein at least 97% of the isobutene, at least 90% of the 1-butene and at least 80% of the 2-butene of the initial olefinic cut are converted to dimers and trimers.

6. A process according to claim 1, wherein:
(a) the charge consisting essentially of an olefinic $C_4$ cut, generally containing isobutane, n-butane, 1- and 2-butenes and isobutene, is fed to said first catalytic polymerization zone;
(b) the effluent from the first catalytic polymerization zone is fed to fractionation in a fractionation zone wherefrom a gasoline consisting of $C_4$ olefins dimers and trimers is recovered separate from a mixture of isobutene, 1- and 2-butenes and paraffinic hydrocarbons which is recovered from the fractionation;
(c) the mixture of isobutene, 1- and 2-butenes and paraffinic hydrocarbons from step (b) is divided into two parts, the first part, of at most 30% by weight of said mixture being removed or fed to the gasoline pool, the second part of said mixture being fed to the second catalytic polymerization zone;
(d) said second part of the mixture being fed to the second catalytic polymerization zone being treated in said zone; and
(e) supplying the effluent from the second catalytic polymerization zone to said fractionation zone.

7. A process according to claim 1, 2, 3 or 4, wherein:
(a) the charge, consisting essentially of an olefinic $C_4$ cut, generally containing isobutane, n-butane, 1- and 2-butenes and isobutene, is fed to said first catalytic polymerization zone;
(b) the effluent from said first catalytic polymerization zone is fed to the fractionation zone wherefrom a gasoline consisting of $C_4$ olefins dimers and trimers is recovered separate from a mixture of isobutene, 1- and 2-butenes and paraffinic hydrocarbons also recovered therefrom;
(c) the mixture of isobutene, 1- and 2-butenes and paraffinic hydrocarbons are treated in a second catalytic polymerization zone;
(d) the effluent from said second catalytic polymerization zone is fractionated in a second fractionation zone;
(e) $C_4$ olefins dimers and trimers are recovered from said second fractionation zone separate from a mixture of paraffinic hydrocarbons with unreacted olefins also recovered from said second fractionation zone; and
(f) the recovered mixture of paraffinic hydrocarbons with unreacted olefins from step (e) is divided into two parts, a first part of at most 30% by weight of said mixture being removed or fed to the gasoline pool, and a second part being recycled to the second catalytic polymerization zone.

8. A process according to claim 1, wherein the catalyst used in the process is a catalyst obtained by treatment of a transition alumina by means of at least one fluorine acid derivative, and with addition of a silicic ester.

9. A process according to claim 1, wherein the catalyst employed is a silica alumina with a silica content of 60–95% by weight.

10. A process according to claim 9, wherein the catalyst has a silica content of 70–90% by weight, and includes 0.1–0.5% of at least one of chromium oxide and zinc oxide.

11. A process according to claim 9, wherein the specific surface of the silica alumina is 50–500 $m^2$ per gram and has a pore volume of 0.40–0.90 cc/gm.

12. A process according to claim 10, wherein the specific surface of the silica alumina is 50–500 $m^2$ per gram and has a pore volume of 0.40–0.90 cc/gm.

* * * * *